United States Patent [19]

Cook

[11] 4,411,263
[45] Oct. 25, 1983

[54] INFANT EYE SHIELD

[76] Inventor: Gayle Cook, 8180 Forestdale Dr., Charlotte, N.C. 28212

[21] Appl. No.: 305,025

[22] Filed: Sep. 23, 1981

[51] Int. Cl.³ ............................................. A61F 13/00
[52] U.S. Cl. ................................. 128/132 R; 128/380; 2/15
[58] Field of Search ................... 128/76.5, 132 R, 163, 128/380, DIG. 15; 2/12, 15, 427, 428, 431, 439, 440, 442, 445, 446, 448; 351/110, 111

[56] References Cited

U.S. PATENT DOCUMENTS

| | | | |
|---|---|---|---|
| 2,671,898 | 3/1954 | Wade | 128/132 R |
| 3,092,103 | 6/1963 | Mower | 128/132 R |
| 3,952,735 | 4/1976 | Wirtschafter et al. | 128/132 R |
| 4,009,494 | 3/1977 | Nusbaum | 128/132 R |
| 4,074,397 | 2/1978 | Rosin | 128/DIG. 15 |
| 4,122,847 | 10/1978 | Craig | 128/132 R |
| 4,331,136 | 5/1982 | Russell et al. | 128/163 |

Primary Examiner—Kyle L. Howell
Assistant Examiner—Max F. Hindenburg
Attorney, Agent, or Firm—Kenneth T. Theodore

[57] ABSTRACT

The invention is an Infant Eye Shield specifically used to protect the eyes of premature and full term infants requiring phototherapy treatment. The shield is constructed to be of the absolute minimum size to expose the greatest amount of skin area to the light rays. It is adhesively attached to the infant for ease of removal without injury to the sensitive skin. The shield is intended to be reuseable but its low cost permits disposable use.

4 Claims, 4 Drawing Figures

U.S. Patent    Oct. 25, 1983    4,411,263
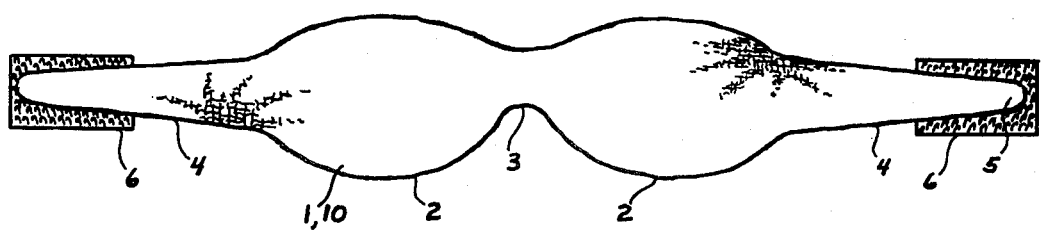
Fig. 1
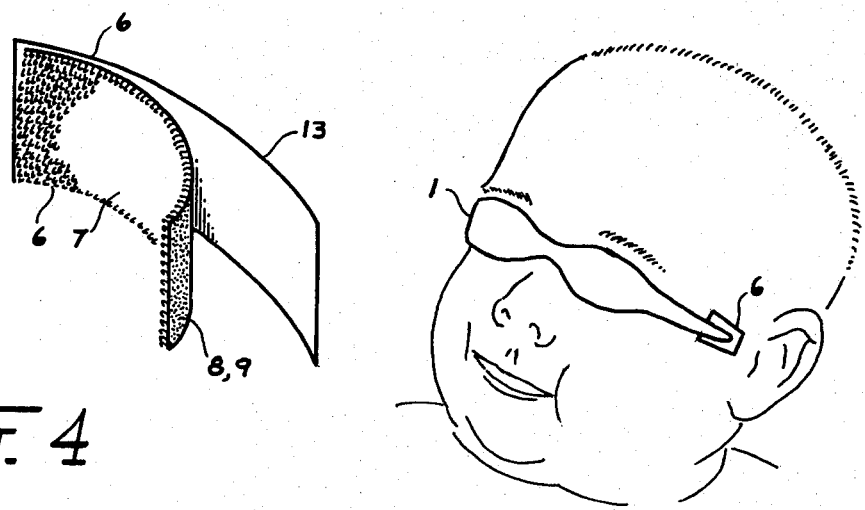
Fig. 4
Fig. 2
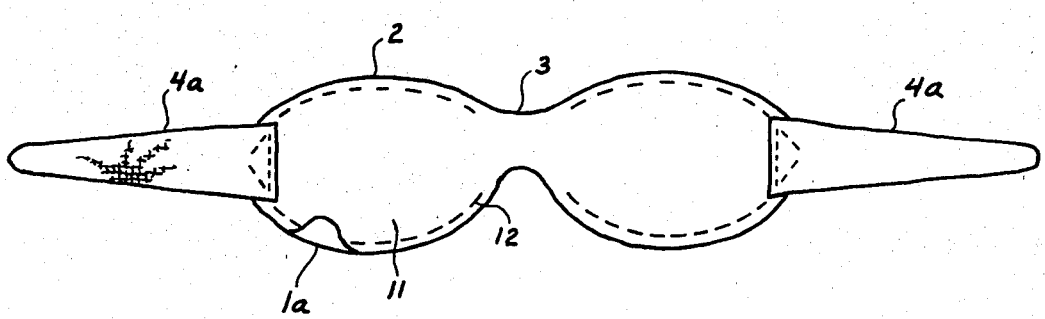
Fig. 3

INFANT EYE SHIELD

BACKGROUND OF THE INVENTION

1. Field of the Invention

The invention lies within the field of eye shields/eye protectors, specifically those intended for infants requiring phototherapy treatment.

2. Description of Prior Art

Phototherapy treatment of infants require that as much skin area be exposed to the light rays as possible in order that the treatment have maximum effectiveness in counteracting the illness, specifically physiologic jaundice or hyperbilirubinemia. These is no known prior art which incompasses all the features desirable to protect the infant's eyes, i.e., maximum eye protection with minimum skin area coverage, ease of installation on and removal from the infant's head, and low cost.

Presently, nurses attending such infants use gauze pads over the infant's eyes. The gauze is secured with surgical tape placed over the gauze and adhesively secured to the infant's temples.

Inherent disadvantages of this prior art are (1) the quality and quantity of gauze used is susceptible to human judgement, (2) the frequent and necessary changing and removal of gauze injures the infant's skin as the tape is pulled from the temple and (3) the high cost of said prior art.

SUMMARY AND OBJECTS OF THE INVENTION

The invention is a preformed eye shield for infants which covers a minimum amount of skin area. The shield has the general shape of typical eye shields and is made of sterilized flexible material having a soft, nap like fiberous surface. Adhesive tabs, consisting of the hook side of Velcro with pressure sensitive adhesive on the back side thereof, are attached to the infants temples by the use of the adhesive back side. The shield is secured to the infant by the use of temple elements which are singularly attached to the tabs as Velcro hook and loop fastening means.

It is a primary object of the invention to have an eye shield which is of minimum size so as to cover the least possible skin area of an infant under phototherapy treatment.

It is a further object of the invention to provide such an eye shield which will not injure the infant upon removal of same.

Additionally, it is an object of the invention to have a low cost, disposable eye shield which is not susceptible to human error and/or judgement.

It is also an object of the invention to overcome those objections to prior art enumerated above.

BRIEF DESCRIPTION OF THE DRAWINGS

FIG. 1 illustrates the eye shield in a plan view.
FIG. 2 illustrates the eye shield as worn by an infant.
FIG. 3 illustrates a modification to the eye shield in a plan view.
FIG. 4 is a detail of the adhesive tabs.

DESCRIPTION OF THE PREFERRED EMBODIMENT

While the preferred embodiment is illustrated and described below, it is to be understood that variations will be apparent to those skilled in the art without departing from the principles of the invention. Accordingly, the invention is not to be limited to the specific form as described and illustrated but rather is to be limited only by a literal interpretation of the claims appended herein.

FIG. 1 illustrates the invention, a one piece Infant Eye Shield 1 consisting of an eye piece 10 of two generally oval shaped protective areas 2 which are joined together by a bridge area 3. Said protective areas 2 are sized to cover the infant's eye and the area immediately surrounding the eye, approximately ¾ inch by 1 inch in size. Said bridge area 3 fits over the infant's nose.

Radiating outwardly from each protective area 2 is a temple element 4 of a general triangular shape terminating at its apex in an element end 5.

Removably attached to the skin side of each said end 5 is an adhesive tab 6. The materials used for said tab 6 and temple elements 4 below are used in combination to form a VELCRO type fastener as known in the art. This type of fastener consists of two material forms; one having a multiplicity of small hooks on its surface and known as the 'hook portion', and the other having a soft nap-like, fiberous material with a multiplicity of small thread-like loops on its surface and known as the 'loop portion'. The joining or pressing together of these surfaces causes said hooks to engage said loops, whereby the surfaces are securely fastened together. The surfaces are seperable by manually peeling one material away from the other. Said tab 6 is detailed in FIG. 4 and consists of the hook portion 7 of a Velcro fastener on one side thereof and self sticking adhesive 8 on the opposite side thereof, the latter side designated as the skin side 9 and the former designated as the outer side of said tab 6. An easily removable piece of waxed paper 13 covers said adhesive 8 during storage and manufacturing to prevent the drying out and/or contamination of the adhesive 8 prior to use. The ends 5, as described below, act as the loop side of a Velcro fastener.

The material used in the shield 1 is sterilized cloth having a soft nap like fiberous material resembling the loop portion of a Velcro fastening means. The major consideration for the material is that it be light proof, (a maximum of 3% light transmissability), from the phototherapy light, thereby insuring protection to the infant's eyes. The material may be multiple layers to insure the light proof requirement. The nap and hook portion 7 is selected so that the ratio of peel strength to shear strength is less than unity. This ratio insures that the shield 1 can easily be peeled from said tab 6 when desired while maintaining a high resistance to being pulled off as the infant turns his head against the bed clothing.

The adhesive 8 selected has a higher peel strength than that of the Velcro fastening device. This insures that when peeling said shield 1 from said tab 6, the tab 6 remains attached to the infant. Additionally, the adhesive 8 has sufficient shear capability to secure the shield 1 to the infant while its peel strength is such that the tab 6 is easily peeled from the infants skin without injury thereto. It's this unique combination of peel vs shear strength between the adhesive 8, hook portion 7, and nap like material which insures the inventions safety and useability.

Placement of said shield 1 on the infant is illustrated in FIG. 2 and described below. The nurse removes the waxed paper 13 from said tabs 6 and gently but firmly attaches the tab 6 skin side to the temple areas of the infant. The shield 1 is then centered over the infant's eyes. Said ends 5 are then attached to the tabs 6 via the hook portion 7 such that the shield 1 is snug but not uncomfortably tight on the infant. Said end 5 is to lie wholly on said tab 6 and not extend over thereof. This insures that an extended end 5 is not caught and rolled off (peeled) a tab 6 as an infant rolls his head (and said end 5) against the bed clothing.

FIG. 3 is a plan view of a modified eye shield 1a which differs only in that it's not one piece construction but requires separate temple elements 4a to be securely attached to the outer ends of said protective areas 2. Said elements 4a are similar in form, fit and function as to said elements 4 and require the use of said tabs 6 as described above. The attachment of said elements 4a to said areas 2 is by sewing.

The advantage of said shield 1a is the possibility of using different materials for said elements 4a and said areas 2, 3. In all instances the elements 4a will be of the same soft nap like material described above wherein said areas 2, 3 are constructed of less expensive gauze like material which is also light proof. An additional material for said areas 2, 3 is plastic film 11 which is specifically coated to be light proof. Additionally, combinations of said film 11 and gauze like material can be used for said areas 2, 3 by simply attaching or stitching 12 the combinations together as illustrated in FIG. 3.

Having thus described my invention, what I claim is:

1. An infant eye shield, for protecting an infants' eyes from phototherapy treatment light, comprising:

an eye piece having two oval shaped protective areas which fit over the infants' eyes, a bridge area which fits over the infant's nose and interconnects said protective areas, and two temple elements oppositely connected to and radiating outwardly from said protective areas for placement over the infant's temples, wherein said temple elements are made of material with small thread-like loops thereon; and individual adhesive tabs having, a skin side with self sticking adhesive thereon for removably adhering to the infant's skin at each temple area, and an outer side having a multiplicity of small hooks thereon, such that said eye piece is removably secured to the infant by engaging said loops of said temple onto said hooks when said tabs are removably attached to the infants' temples, wherein said shield covers a minimum area of the infant's facial skin.

2. The invention of claim 1 wherein the material of said eye piece is of light proof material.

3. The invention of claim 1 wherein said adhesive has a slightly higher peel strength than that of said loop and hook engagement to insure easy removal of said eye piece without removal of said tabs.

4. The invention of claim 3 wherein said eye piece is constructed of light proof plastic film.

* * * * *